United States Patent [19]

Breuninger et al.

[11] Patent Number: 4,694,084
[45] Date of Patent: Sep. 15, 1987

[54] GLYCEROL ETHER PHOSPHATIDES

[75] Inventors: Manfred Breuninger, Freiburg, Fed. Rep. of Germany; Dieter Schmidt, Basel, Switzerland

[73] Assignee: Hoffmann-La Roche Inc., Nutley, N.J.

[21] Appl. No.: 709,871

[22] Filed: Mar. 8, 1985

[30] Foreign Application Priority Data

Mar. 15, 1984 [CH] Switzerland .......................... 1287/84
Feb. 4, 1985 [CH] Switzerland ............................ 491/85

[51] Int. Cl.$^4$ .......................... C07F 9/58; C07F 9/65; C07F 9/10
[52] U.S. Cl. ...................................... 546/25; 540/542; 548/413; 558/169
[58] Field of Search .......................... 558/169; 546/25; 540/542; 548/413

[56] References Cited

U.S. PATENT DOCUMENTS

| | | | |
|---|---|---|---|
| 4,158,707 | 6/1979 | Steffen et al. | 424/244 |
| 4,411,894 | 10/1983 | Schrank et al. | 424/199 |
| 4,562,005 | 12/1985 | Nojima et al. | 558/169 |

FOREIGN PATENT DOCUMENTS 163389 9/1984 Japan .
2020663 11/1979 United Kingdom .

OTHER PUBLICATIONS

CA 92:197869u (1980).
Vaver et al., Biorg. Khim. (1980).

*Primary Examiner*—Anton H. Sutto
*Attorney, Agent, or Firm*—Jon S. Saxe; Bernard S. Leon; Matthew Boxer

[57] ABSTRACT

Compounds of the general formula

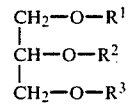

wherein two of the residues $R^1$, $R^2$ and $R^3$ represent $C_{10-30}$-alkyl residues with at least 8 C-atoms in a straight chain, at least one of these residues being substituted by at least 2 $C_{1-3}$-alkyl residues and the sum of the C-atoms in the two residues being greater than 20; and the third residue is a residue $-P(O)(O^-)OR^4$ in which $R^4$ represents a lower-alkyl or $C_{5-7}$-cycloalkyl residue which is substituted by a quaternary ammonium group or a $C_{5-7}$-cycloalkyl residue which contains a di-(lower-alkyl)-substituted nitrogen atom, are useful for the manufacture of colloidal solution systems. The compounds of formula I can be prepared starting from glycerol derivatives as described in more detail in the specification.

7 Claims, No Drawings

GLYCEROL ETHER PHOSPHATIDES

DESCRIPTION OF THE INVENTION

The invention is concerned with novel glycerol ether phosphatides of the general formula

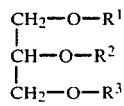

wherein two of the residues $R^1$, $R^2$ and $R^3$ represent $C_{10-30}$-alkyl residues with at least 8 C-atoms in a straight chain, at least one of these residues being substituted by at least 2 $C_{1-3}$-alkyl residues and the sum of the C-atoms in the two residues being greater than 20; and the third residue is a residue $-P(O)(O^-)OR^4$ in which $R^4$ represents a lower-alkyl or $C_{5-7}$-cycloalkyl residue which is substituted by a quaternary ammonium group or a $C_{5-7}$-cycloalkyl residue which contains a di-(lower-alkyl)-substituted nitrogen atom.

The alkyl residues $R^1$, $R^2$ and $R^3$ are preferably terpene hydrocarbon residues. Examples of such terpene hydrocarbon residues are residues of the formula

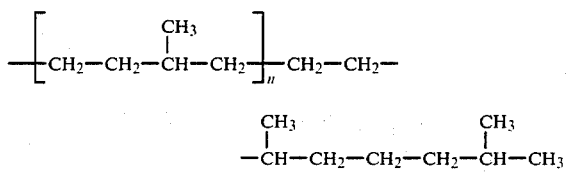

wherein n is a whole number of 0–4, such as tetrahydrogeranyl, hexahydrofarnesyl and especially dihydrophytyl.

Examples of residues $R^3$ are tri-(lower-alkyl)ammonio-lower-alkyl such as trimethylammonioethyl and trimethylammoniobutyl; tri-(lower-alkyl)-ammonio-$C_{5-7}$-cycloalkyl such as trimethylammoniocyclohexyl; and N,N-di-lower-alkyl-$C_{4-6}$-azacycloalkyl such as N,N-dimethylpiperidyl. The quaternary ammonium group present in residue $R^3$ can also be formed by a nitrogen atom of a 5–7-membered heterocyclic ring. Examples of such residues $R^3$ are (N-lower-alkyl-piperidyl)-lower-alkyl such as (N-methylpiperidinyl)-ethyl. The term "lower" denotes, in particular, residues with 1–6 C-atoms such as methyl, ethyl, propyl, butyl.

A preferred group of compounds of formula I comprises those in which $R^1$ and $R^2$ represent $C_{10-30}$-alkyl residues with at least 8 C-atoms in a straight-chain, which are each substituted by at least 2 $C_{1-3}$-alkyl residues.

Preferred residues $R^4$ are 2-(trimethylammonio)ethyl, 4-(trimethylammonio)butyl, 4-(trimethylammonio)cyclohexyl and N,N-dimethyl-4-piperidyl.

The compounds of formula I can be manufactured in accordance with the invention by reacting a glycerol ether of the general formula

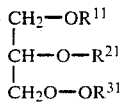

wherein one of the residues $R^{11}$, $R^{21}$ and $R^{31}$ represents hydrogen and the remaining residues represent a $C_{10-30}$-alkyl residue as defined above.

(a) with phosphorus oxychloride in the presence of a base and thereafter with an alcohol $R^4OH$, wherein $R^4$ has the significance given above, or (b) in the presence of a base with a compound of the formula

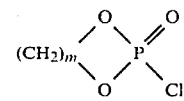

wherein m is 2 or 3,
and thereafter with a tri-lower alkylamine.

As bases there come into consideration especially organic bases, e.g. tertiary amines such as triethylamine, pyridine or collidine. The reaction is conveniently carried out in a inert organic solvent, e.g. a hydrocarbon such as benzene or toluene or a chlorinated hydrocarbon such as chloroform. The reaction is conveniently carried out at low temperatures, e.g. at 0° C. to room temperature, whereby in the case of the reaction of a compound II with phosphorus oxychloride the latter is conveniently added at low temperatures, e.g. at −78° C. to −10° C.

The compounds of formula I can be used for the manufacture of colloidal solution systems such as liposome and mixed micelle solutions, e.g. for the solubilization of fat-soluble medicaments in aqueous systems in a similar manner to natural lecithins.

Compared with natural lecithins the novel compounds of formula I have e.g. the advantage of a greater chemical stability. Furthermore, in contrast to natural lecithins they can be manufactured in a chemically uniform form.

For the manufacture of mixed micelles the novel compounds can be combined especially with cholanic acids and their salts, e.g. cholic acid, glycocholic acid, taurocholic acid, deoxychloric acid, glycodeoxycholic acid, chenodeoxycholic acid.

The liposome and mixed micelle solutions which can be manufactured based on the compounds in accordance with the invention can be used for the solubilization of pharmaceuticals which are difficultly soluble in water or insoluble in water, e.g. benzodiazepines such as diazepam, nitrazepam, flunitrazepam, medazepam and bromazepam, or fat-soluble vitamins such as vitamin A, D, E and K. The liposome solutions which can be manufactured based on the compounds in accordance with the invention can contain sugars, e.g. mono- or disaccharides such as glucose, fructose, or saccarose; or sugar-like polyalcohols such as sorbitol or xylol, in order to improve the stability.

The compounds of formula I exist as internal salts. They contain chiral centres and can therefor exist in various enantiomeric forms, which are likewise an object of the invention.

The compounds of formula II can be prepared starting from glycerol derivatives wherein one or two hydroxy groups are protected as is described in more detail in the Examples.

The invention is illustrated further by the following Examples.

EXAMPLE 1

8.4 mmol of triethylamine (distilled over KOH) in 5 ml of chloroform (dried over aluminum oxide) were treated at −78° C. while stirring with 2.2 mmol of freshly distilled phosphorus oxychloride. The cooling bath was replaced by an ice-bath and thereafter 2.09 mmol of (RS)-2,3-bis-[[(3RS,7R,11R)-3,7,11,15-tetramethylhexadecyl]oxy]propanol dissolved in 10 ml of dry chloroform were added dropwise. Thereafter, the mixture was stirred without further cooling for 1 hour. After cooling again to 0° C. 3.2 mmol of choline tosylate in about 20 ml of dry pyridine were added while stirring in the course of about 20 minutes. Thereafter, the reaction mixture was stirred at room temperature for several hours and then left to stand overnight. For the working-up, the chloroform was removed at 30° C. in a water-jet vacuum, the residue was treated with 20 mmol of potassium hydrogen carbonate and 5 ml of water and the mixture was evaporated to dryness in a water-jet vacuum. The residue was taken up in dichloromethane, treated with toluene, filtered and evaporated in a water-jet vacuum. The residue is about 30 ml of tetrahydrofuran-water (95:5) was passed several times slowly over a column containing 25 g of ion exchanger Amberlite MB-83. Thereafter, the ion exchanger was washed well with the same solvent. The filtrate and wash solution were evaporated in a water-jet vacuum, water residues were removed by evaporation with ethanol. The thus-obtained crude product was chromatographed on 100 g of silica gel. Using chloroform/methanol (7:3) there were obtained coloured impurities, thereafter using chloroform/methanol/water (60:35:5) there was obtained the reaction product, O-[[(RS)-2,3-bis[[(3RS,7R,11R)-3,7,11,15-tetramethylhexadecyl]oxy]propyl]hydroxyphosphinyl]choline hydroxide (internal salt).

NMR: 0.75-0.95 (multiplet, $CH_3$) 1.0-1.8 (broad multiplet, $CH_2$ and CH) 3.39 (broad single, $CH_3$—N) 3.3-3.7, 3.7-4.1 and 4.1-4.5 (3 broad multiplets, $CH_2$—N, $CH_2$—O and CH—O).

Elementary analysis for $C_{48}H_{100}NO_6P$: Calculated: C 70.45; H 12.32; N 1.71. Found: C 70.44; H 12.63; N 1.82 (3.04% water).

The starting material can be prepared as follows:

(a) 50 mmol of dimethylaminoethanol in 25 ml of dry ether were treated with a solution of 50 mmol of methyl p-toluenesulphonate in 50 ml of dry ether. The reaction mixture was left to stand at room temperature overnight with the exclusion of moisture. The choline tosylate was filtered off under suction with the exclusion of moisture, washed with dry ether and stored dry.

(b) A solution of 1.0 mol of dihydrophytol in 1500 ml of dry dichloromethane was treated while stirring with 300 ml of dry pyridine and 1.1 mol of toluenesulphochloride. The solution was left to stand at room temperature overnight, the majority of the solvent was thereafter distilled off at 30° (bath temperature) and the residue was taken up in ether. The solution was concentrated, treated with 200 ml of water, 100 g of solution hydrogen carbonate and 100 ml of pyridine and stirred for 1 hour. Thereafter, the solution was evaporated to dryness at 60° C., the residue was treated with 1000 ml of toluene and the toluene was distilled off under reduced pressure. The residue was taken up in 500 ml of toluene, the solution was filtered and the solvent was removed, there being obtained (3RS,7R,11R)-3,7,11,15-tetramethylhexadecyl p-toluenesulphonate.

(c) 0.8 g of sodium hydride (80%) was washed twice with 10 ml of pentane and treated with 80 ml of dimethylformamide and 1.8 g of 1-O-benzylglycerol in 10 ml of dimethylformamide. The reaction mixture was stirred at 50°-60° C. for 1 hour with the exclusion of moisture, treated with 22 mmol of (3RS,7R,11R)-3,7,11,15-tetramethylhexadecyl p-toluenesulphonate in 20 ml of dimethylformamide and stirred at 50°-60° C. for 1-4 hours. Thereafter, 5 ml of water and 20 ml of ethanol were added, the solvent was distilled off at 60° C. in a water-jet vacuum and the residue was taken up in either. After working-up the ethereal solution was obtained (RS)-1-(benzyloxy)-2,3-bis[[(3RS,7R,11R)-3,7,11,15-tetramethylhexadecyl]oxy]propane as a colourless oil.

(d) 4 g (5.4 mmol) of the benzyl ether obtained in paragraph (c) in a mixture of 25 ml of tetrahydrofuran and 25 ml of ether were hydrogenated over 0.2 g of Pd-C (5%) and gave, after chromatography, (RS)-2,3-bis[[(3RS,7R,11R)-3,7,11,15-tetramethylhexadecyl]oxy]propanol.

EXAMPLE 2

In analogy to Example 1, from 1 g (1.9 mmol) of (RS)-2,3-bis[[(3RS,7RS)-3,7,11-trimethyldodecyl]oxy]propanol and 1 g (3.6 mmol) of choline tosylate there was obtained 0.69 g (52.9%) of O-[[(RS)-2,3-bis[[(3RS,7RS)-3,7,11-trimethyldodecyl]oxy]propoxy]hydroxyphosphinyl]choline hydroxide (internal salt).

NMR: 0.8-0.95 (multiplex $CH_3$), 1.05-1.80 (broad multiplet, $CH_2$ and CH), 3.21 (singlet, $CH_3$—N), 3.38-4.45 (broad multiplet, $CH_2$—N, $CH_2$—O and CH—O).

Elementary analysis for $C_{38}H_{80}NO_6P$: Calculated: C 67.32; H 11.89; N 2.07. Found: C 67.13; H 11.90; N 2.03 (2.53% water).

The propanol derivative used as the starting material can be obtained starting from hexahydrofarnesol in analogy to Example 1, paragraph (b), (c) and (d).

EXAMPLE 3

In analogy to Example 1, from 0.9 g (2.4 mmol) of (RS)-2,3-bis[[(3RS,7RS)-3,7,11-trimethyldodecyl]oxy]propanol and 1.2 g (3.95 mmol) of (4-hydroxybutyl)-trimethylammonium p-toluenesulphonate there were obtained 0.3 g (17.6%) of [4-[[[(RS)-2,3-bis[[(3RS,7RS)-3,7,11-trimethyldodecyl]oxy]propoxy]hydroxyphosphinyl]oxy]butyl]trimethylammonium hydroxide (internal salt).

NMR: 0.78-0.90 (multiplet, $CH_3$), 1.05-2.13 (broad multiplet, $CH_2$ and CH), 3.14 (singlet, $CH_3$—N), 3.40-4.13 (broad multiplet, $CH_2$—N, $CH_2$—O and CH—O).

Elementary analysis for $C_{40}H_{84}NO_6P$: Calculated: C 68.04; H 11.99; N 1.98. Found: C 67.70; H 12.26; N 2.07 (1.31% water).

EXAMPLE 4

From 1 g (1.7 mmol) of (RS)-1-O-[(3RS,7R,11R)-3,7,11,15-tetramethylhexadecyl]-2-O-[(3RS,7RS)-3,7,11-trimethyldodecyl]-glycerol and 0.7 g (2.6 mmol) of choline tosylate there was obtained 0.9 g (70.14%) of O-[hydroxy](RS)-3-[[(3RS,7RS)-3,7,11,15-trimethyldodecyl]oxy]propoxy]phosphinyl]choline hydroxide (internal salt).

NMR: 0.80-0.97 (multiplet, $CH_3$), 1.06-1.82 (broad multiplet, $CH_2$ and CH), 3.22 (singlet, $CH_3$—N), 3.38–3.78, 3.78–4.06 and 4.06–4.44 (3 broad multiplets, CH$_2$—N, CH$_2$—O and CH—O).

Elementary analysis for C$_{43}$H$_{90}$NO$_6$P: Calculated: C 69.02; H 12.13; N 1.87. Found: C 68.69; H 11.94; N 2.24 (0.80% water).

The glycerol derivative used as the starting material can be prepared as follows:

(a) 5.25 g (175 mmol) of sodium hydride (80%) were washed twice with 10 ml of pentane. Thereafter, 400 ml of dimethylformamide and 120 mmol of isopropylideneglycerol were added. The reaction mixture was stirred at 60° C. for 1 hour. After cooling to room temperature 100 mmol of (3RS,7R,11R)-3,7,11,15-tetramethylhexadecyl p-toluenesulphonate in 100 ml of dimethylformamide were added. The reaction mixture was stirred at 60° C. for 2 hours. After the addition of a small amount of water the majority of the solvent was removed at 65° C. The residue was suspended in toluene, filtered and freed from solvent. After chromatography of the crude product on silica gel there was obtained (RS)-2,2-dimethyl-4-[[[(3RS,7R,11R)-3,7,11,15-tetramethylhexadecyl]oxy]methyl]-1,3-dioxolane.

(b) 100 mmol of the dioxolane obtained in accordance with (a) were dissolved in 100 ml of dioxan, treated with 10 ml of 1N HCl and heated under reflux for 1 hour. Thereafter, the solvent was removed, water residues were removed with toluene and the crude product was chromatographed on silica gel. A byproduct was removed with hexane/ether. The (RS)-1-O-[(3RS,7R,11R)-3,7,15-tetramethylhexadecyl]glycerol, a colourless oil, was eluted with ethyl acetate.

(c) 100 mmol of the glycerol derivative obtained in (b) in 10 ml of pyridine were reacted at room temperature overnight with 101 mmol of trityl chloride. The pyridine was removed under reduced pressure and the residue was taken up in 100 ml of ether. The solution was filtered, the ether was removed and the residue was treated with 10 ml of pyridine, 1 ml of water and 1 g of potassium bicarbonate and stirred at room temperature for 1 hour. The solvent was removed under reduced pressure and moisture residues were removed with toluene. The residue was taken up in toluene and chromatographed on silica gel with ether/pyridine (99:1). There was obtained (RS)-1-O-[3RS,7R,11R)-3,7,11,15-tetramethylhexadecyl]-3-O-tritylglycerol as an oil.

(d) 4.5 g (150 mmol) of sodium hydride were washed twice with pentane and treated with 300 ml of dimethylformamide and 100 mmol of the tritylglycerol obtained in accordance with (c). After stirring for one hour at 60° C. the reaction mixture was cooled and treated with about 120 mmol of (3RS,7RS)-3,7,11-trimethyldodecyl p-toluenesulphonate. The reaction mixture was stirred at 60° C. for 2 hours, the solvent was removed at 70° C. and the crude product was chromatographed on silica gel with hexane/ether (4:1), there being obtained (RS)-1-O-[(3RS,7R,11R)-3,7,11,15-tetramethylhexadecyl]-2-O-[(3RS,7RS)-3,7,11-trimethyldodecyl]-3-O-tritylglycerol.

(e) 100 mmol of the tritylglycerol obtained in accordance with (d) were dissolved in 100 ml of dioxan and 10 ml of 1N HCl and heated under reflux for 1 hour. The solvent was removed, water residues were removed with toluene and the residue was taken up in petroleum ether. The triphenylmethanol was crystallized out at −20° C. and filtered off. The concentrated filtrate was chromatographed on silica gel with hexane/ether (4:1). There was obtained (RS)-1-O-[(3RS,7R,11R)-3,7,11,15-tetramethylhexadecyl]-2-O-[(3RS,7RS)-3,7,11-trimethyldodecyl]glycerol as a colourless oil.

EXAMPLE 5

In analogy to Example 1, from 1.2 g (2.3 mmol) of (RS)-2-O-[(RS)-3,7-dimethyloctyl]-1-O-[(3RS,7R,11R)-3,7,11,15-tetramethylhexadecyl]glycerol and 0.97 g (3.5 mmol of choline tosylate, there was obtained 0.95 g (59.8%) of O-[hydroxy[(RS)-3-[[(3RS,7R,11R)-3,7,11,15-tetramethylhexadecyl]oxy]-2-[[(RS)-3,7-dimethyloctyl]oxy]propoxy]phosphinyl]chlorine hydroxide (internal salt).

NMR: 0.8–0.95 (multiplet, CH$_3$), 1.05–1.80 (broad multiplet, CH$_2$ and CH), 3.25 (singlet, CH$_3$—N), 3.40–4.5 (broad multiplet, CH$_2$-N, CH$_2$-N and CH—O).

Elementary analysis for C$_{38}$H$_{50}$NO$_6$P: Calculated: C 67.32; H 11.89; N 2.07. Found: C 67.42; H 11.65; N 2.05 (1.57% water).

The starting material was prepared from (RS)-1-O-[(3RS,7R,11R)-3,7,11,15-tetramethylhexadecyl]-3-O-tritylglycerol and (RS)-3,7-dimethyloctyl p-toluenesulphonate in analogy to Example 4(d) and (e).

EXAMPLE 6

In analogy to Example 1, from 0.91 g (1.56 mmol) of (RS)-2-O-[(3RS,7R,11R)-3,7,11,15-tetramethylhexadecyl]-1-O-[(3RS,7RS)-3,7,11-trimethyldodecyl]glycerol and 0.64 g (2.3 mmol) of choline tosylate there was obtained 0.82 g (70.2%) of O-[hydroxy[(RS)-2-[[(3RS,7R,11R)-3,7,11,15-tetramethylhexadecyl]oxy]-3-[[(3RS,7RS)-3,7,11-trimethyldodecyl]oxy]propoxy]phosphinyl]choline hydroxide (internal salt).

NMR: 0.77–1.00 (multiplet, CH$_3$), 1.05–1.90 (broad multiplet, CH$_2$ and CH), 3.25 (singlet, CH$_2$—N), 3.38–3.78 3.78–4.00 and 4.00–4.44 (3 multiplets, CH$_2$—N, CH$_2$—O and CH—O).

Elementary analysis for C$_{43}$H$_{90}$NO$_6$P: Calculated: C 69.03; H 12.13; N 1.87. Found: C 68.87; H 12.29; N 2.00 (1.52% water).

The starting material was prepared from (RS)-1-O-[(3RS,7RS)-3,7,11-trimethyldodecyl]-3-O-tritylglycerol and (3RS,7R,11R)-3,7,11,15-tetramethylhexadecyl p-toluenesulphonate in analogy to Example 4(d) and (e).

EXAMPLE 7

In analogy to Example 1, from 1 g (2.26 mmol) of (RS)-2-O-[(RS)-3,7-dimethyloctyl]-1-O-[(3RS,7RS)-3,7,11-trimethyldodecyl]glycerol and 0.93 g (3.4 mmol) of choline tosylate there was obtained 0.9 g (65.6%) of O-[hydroxy[(RS)-3-[[(3RS,7RS)-3,7,11-trimethyldodecyl]]oxy]-2-[[(RS)-3,7-dimethyloctyl]oxy]propoxy]phosphinyl]choline hydroxide (internal salt).

NMR: 0.8–0.95 (multiplet, CH$_3$), 1.05–1.88 (broad multiplet, CH$_2$ and CH), 3.26 (singlet, CH$_3$—N, 3.41–3.8, 3.8–4.06 and 4.06–4.44 (3 multiplets, CH$_2$—N, CH$_2$—O and CH—O).

Elementary analysis for C$_{33}$H$_{70}$NO$_6$P: Calculated: C 65.20; H 11.61; N 2.30. Found: C 64.82; H 11.35; N 2.31 (2.14% water).

The starting material was prepared from (RS)-1-O-[(3RS,7RS)-3,7,11-trimethyldodecyl]-3-O-tritylglycerol and (RS)-3,7-dimethyloctyl p-toluenesulphonate in analogy to Example 4(d) and (e).

EXAMPLE 8

In analogy to Example 1, from 1 g (1.9 mmol) of (RS)-1-O-[(RS)-3,7-dimethyloctyl]-2-O-

[(3RS,7RS,11RS)-3,7,11,15-tetramethylhexadecyl]-glycerol and 0.75 g (2.7 mmol) of choline tosylate there were obtained 600 mg (46%) of O-[hydroxy[(RS)-2-[[(3RS,7RS,11RS)-3,7,11,15-tetramethylhexadecyl]oxyl]-3-[[(RS)-3,7-dimethyloctyl]ocy]propoxy]phosphinyl]choline hydroxide (internal salt).

NMR: 0.8–0.95 (multiplet, CH$_3$), 1.05–1.75 (broad multiplet, CH$_2$ and CH), 3.38 (broad singlet, CH$_3$—N) and 3.3–4.5 (broad multiplet, CH$_2$—N, CH$_2$—O and CH—O).

Elementary analysis for C$_{38}$H$_{80}$NO$_6$P: Calculated: C 67.32; H 11.89; N 2.07. Found: C 66.86; H 12.11; N 1.94 (1.90% water).

The starting material was prepared from (RS)-1-O-[(RS)-3,7-dimethyloctyl]-3-O-tritylglycerol and (3RS,7RS,11RS)-3,7,11,15-tetramethylhexadecyl p-toluenesulphonate in analogy to Example 4(d) and (e).

EXAMPLE 9

In analogy to Example 1, from 1 g (1.9 mmol) of (RS)-1-O-[(RS)-dimethyloctyl]-2-[(3RS,7RS)-3,7,11-trimethyldodecyl]glycerol and 1.5 g (5.5 mmol) of choline tosylate there was obtained 0.82 g (60.2%) of O-[hydroxy[(RS)-2-[[(RS,7RS0-3,7,11-trimethyldodecyl]oxy]propoxy]phosphinyl]choline hydroxide (internal salt).

NMR: 0.75–0.96 (multiplet, CH$_3$), 1.05–1.81 (broad multiplet, CH$_2$ and CH), 3.42 (broad singlet, CH$_3$—N), 3.3–4.56 (broad multiplet, CH$_2$—N, CH$_2$—O and CH—O).

Elementary analysis for C$_{33}$H$_{70}$NO$_6$P: Calculated: C 65.20; H 11.61; N 2.30. Found: C 65.56; H 11.90; N 2.29 (1.57% water).

The starting material was prepared from (RS)-1-O-[(RS)-3,7-dimethyloctyl]-3-O-tritylglycerol and (3RS,7RS)-3,7,11-trimethyldodecyl p-toluenesulphonate in analogy to Example 4(d) and (e).

EXAMPLE 10

In analogy to Example 1, from 1 g (1.53 mmol) of (RS)-2,3-bis-[[(3RS,7R,11R)-3,7,11,15-tetramethylhexadecyl]oxy]propanol and 0.7 g (2.3 mmol) of (4-hydroxybutyl)-trimethylammonium p-toluenesulphonate there was obtained 0.78 g (60.2%) of [4-[[[(RS)-2,3-bis[[(3RS,7RS,11R)-3,7,11,15-tetramethylhexadecyl]oxy]propoxy]hydroxyphosphinyl]oxy]butyl]trimethylammonium hydroxide (internal salt).

NMR: 0.78–0.95 (multiplet, CH$_3$), 1.05–2.11 (broad multiplet, CH$_2$ and CH), 3.11 (singlet, CH$_3$—n), 3.33–4.02 (broad multiplet, CH$_2$—N, CH$_2$—O and CH—O).

Elementary analysis for C$_{50}$H$_{104}$NO$_6$P: Calculated: C 70.96; H 12.39; N 1.65. Found: C 71.20; H 12.34; N 1.84 (0.98% water).

The (4-hydroxybutyl-trimethyl-ammonium p-toluenesulphonate was prepared for 4-dimethylaminobutanol in analogy to Example 1, paragraph (a).

EXAMPLE 11

In analogy to Example 1, from 12 g (18.4 mmol) of (RS)-2,3-bis[[(3RS,7RS,11RS)-3,7,11,15-tetramethylhexadecyl]oxy]propanol and 10.4 g (34.3 mmol) of (4-hydroxybutyl)-trimethylammonium p-toluenesulphonate there were obtained 8 g (51.4%) of [4-[[[(RS)-2,3-bis[[(3RS,7RS,11RS)-3,7,11,15-tetramethylhexadecyl]oxy]propoxy]hydroxyphosphinyl]oxy]butyl]trimethylammonium hydroxide (internal salt).

NMR: Almost identical with the spectrum of the compound of Example 10.

Elementary analysis for C$_{50}$H$_{104}$NO$_6$P: Calculated: C 70.96; H 12.39. Found: C 70.52; H 12.37 (0.25% water).

EXAMPLE 12

In analogy to Example 1, from 1 g (1.71 mmol) of (RS)-1-O-[(3RS,7R,11R)-3,7,11,15-tetramethylhexadecyl]-2-O-[(3RS,7RS)-3,7,11-trimethyldodecyl]-glycerol and 0.78 g (2.6 mmol) of (4-hydroxybutyl)-trimethylammonium p-toluenesulphonate there was obtained 0.83 g of [4-[[[hydroxy-[(RS)-3-[(3RS,7R,11R)-3,7,11,15-tetramethylhexadecyl]oxy]-2-[[3RS,7RS)-3,7,11-trimethyldodecyl]oxy]propoxy]-phosphinyl]oxy]butyl]trimethylammonium hydroxide (internal salt).

NMR: 0.84–0.92 (multiplet, CH$_3$), 1.05–2.10 (broad multiplet, CH$_2$ and CH), 3.12 (singlet, CH$_3$—N), 3.30–4.05 (broad multiplet, CH$_2$—N, CH$_2$—O and CH—O).

Elementary analysis for C$_{45}$H$_{94}$NO$_6$P: Calculated: C 69.63; H 12.21; N 1.80. Found: C 69.71; H 12.48; N 2.17 (1.23% water).

EXAMPLE 13

In analogy to Example 1, from 1.2 g (2.34 mmol) of (RS)-2-O-[(RS)-3,7-dimethyloctyl]-1-O-[(3RS)7R,11R)-3,7,11,15-tetramethylhexadecyl]glycerol and 1.06 g (3.49 mmol) of (4-hydroxybutyl)-trimethylammonium p-toluenesulphonate there was obtained 0.7 g (42.3%) of [4-[[hydroxy-[(RS)-3-[[3RS,7R,11R)-3,7,11,15-tetramethylhexadecyl]oxy]-2-[[(RS)-3,7-dimethyloctyl]oxy]propoxy]phosphinyl]oxy]butyl]trimethylammonium hydroxide (internal salt).

NMR: 0.80–0.97 (multiplet, CH$_3$), 1.05–2.30 (broad multiplet, CH$_2$ and CH), 3.18 (singlet, CH$_3$—N), 3.38–4.15 (broad multiplet, CH$_2$—N, CH$_2$—O and CH—O). Elementary analysis for C$_{40}$H$_{84}$NO$_6$P: Calculated: C 68.04; H 11.99; N 1.98. Found: C 68.37; H 11.77; N 1.99 (2.46% water).

EXAMPLE 14

In analogy to Example 1, from 0.91 g (1.56 mmol) of (RS)-2-O-[(3RS,7R,11R)-3,7,11,15-tetramethylhexadecyl]-1-O-[(3RS,7RS)-3,7,11-trimethyldodecyl]-glycerol and 0.71 g (2.34 mmol) of (4-hydroxybutyl)-trimethylammonium p-toluenesulphonate there was obtained 0.85 g of [4-[[hydroxy-[(RS)-2-[[(3RS,7R,11R)-3,7,11,15-tetramethylhexadecyl]oxy]-3-[[(3RS,7RS)-3,7,11-trimethyldodecyl]oxy]propoxy]-phosphinyl]oxy]butyl]trimethylammonium hydroxide (internal salt).

NMR: 0.80–0.97 (multiplet, CH$_3$), 1.05–2.44 (broad multiplet, CH$_2$ and CH), 3.14 (singlet, CH$_3$—N), 3.38–4.00 (broad multiplet, CH$_2$—N, CH$_2$—O and CH—O).

Elementary analysis for C$_{45}$H$_{94}$NO$_6$P: Calculated: C 69.63; H 12.21; N 1.80. Found: C 69.83; H 11.85; N 1.44 (1.40% water).

EXAMPLE 15

In analogy to Example 1, from 1 g (2.26 mmol) of (RS)-2-O-[(RS)-3,7-dimethyloctyl]-1-O-[(3RS,7RS)-3,7,11-trimethyldodecyl]glycerol and 1.03 g (3.4 mmol) of (4-hydroxybutyl)-trimethylammonium p-toluenesulphonate there was obtained 0.9 g (62.7%) of [4-[[hydroxy-[(RS)-3-[[(3RS,7RS)-3,7,11-trimethyldodecyl- ]oxy]-2-[[(RS)-3,7-dimethyloctyl]oxy]propoxy]phosphinyl]oxy]butyl]trimethylammonium hydroxide (internal salt).

NMR: 0.80–0.97 (multiplet, $CH_3$), 1.05–2.15 (broad multiplet, $CH_2$ and CH), 3.18 (singlet, $CH_3$—N), 3.38–4.10 (broad multiplet, $CH_2$—N, $CH_2$—O and CH—O).

Elementary analysis for $C_{35}H_{74}NO_6P$: Calculated: C 66.10; H 11.73; N 2.20. Found: C 65.61; H 11.43; N 2.19 (1.22% water).

EXAMPLE 16

In analogy to Example 1, from 1 g (1.92 mmol) of (RS)-1-O-[(RS)-3,7-dimethyloctyl]-2-O-[(3RS,7RS,11RS)-3,7,11,15-tetramethylhexadecyl]-glycerol and 1.5 g (4.95 mmol) of (4-hydroxybutyl)-trimethylammonium p-toluenesulphonate there was obtained 0.72 g (53.0%) of [4-[[hydroxy-[(RS)-2-[[(3RS,7RS,11RS)-3,7,11,15-tetramethylhexadecyl]oxy]-3-[[(RS)-3,7-dimethyloctyl]oxy]propoxy]phosphinyl]oxy]butyl]trimethylammonium hydroxide (internal salt).

NMR: 0.80–0.95 (multiplet, $CH_3$), 1.05–2.44 (broad multiplet, $CH_2$ and CH), 3.30 (broad singlet, $CH_3$—N), 3.3–4.1 (broad multiplet, $CH_2$—N, $CH_2$—O and CH—O).

Elementary analysis for $C_{40}H_{84}NO_6P$: Calculated: C 68.04; H 11.99; N 1.98. Found: C 68.12; H 12.44; N 1.95 (1.59% water).

EXAMPLE 17

In analogy to Example 1, from 1 g (2.26 mmol) of (RS)-1-O-[(RS)-dimethyloctyl]-2-O-[(3RS,7RS)-3,7,11-trimethyldodecyl]glycerol and 1.8 g (5.9 mmol) of (4-hydroxybutyl)-trimethylammonium p-toluenesulphonate there was obtained 0.5 g of [4-hydroxy-[(RS)-2-[[(3RS,7RS)-3,7,11-trimethyldodecyl]oxy]-3-[[(RS)-3,7-dimethyloctyl]oxy]propoxy]phosphinyl]oxy]butyl]-trimethylammonium hydroxide (internal salt).

NMR: 0.75–0.95 (multiplet, $CH_3$), 1.05–2.42 (broad multiplet, $CH_2$ and CH), 3.34 (broad singlet, $CH_3$—N), 3.40–4.15 (broad multiplet, $CH_2$—N, $CH_2$—O and CH—O).

Elementary analysis or $C_{35}H_{74}NO_6P$: Calculated: C 66.10; H 11.73; N 2.20. Found: C 66.10; H 11.88; N 2.24 (2.73% water).

EXAMPLE 18

In analogy to Example 1, from 0.9 (1.38 mmol) of (RS)-2,3bis[[(3RS,7R,11R)-3,7,11,15-tetramethylhexadecyl]oxy]propanol and 0.69 g (2.1 mmol) of (4-hydroxycyclohexyl)-trimethylammonium p-toluenesulphonate there was obtained 0.9 g (74.9%) of [(cis/trans)-4[[[(RS)-2,3-bis[[(3RS,7R,11R)-3,7,11,15-tetramethylhexadecyl]oxy]propoxy]hydroxyphosphinyl]oxy]cyclohexyl]trimethylammonium hydroxide (internal salt).

NMR: 0.80–0.96 (multiplet, $CH_3$), 1.05–2.44 (broad multiplet, $CH_2$ and CH), 3.08 (singlet, $CH_3$—N), 3.33–4.0 (broad multiplet, CH—N, $CH_2$—O and CH—O).

Elementary analysis for $C_{52}H_{106}NO_6P$: Calculated: C 71.59; N 12.25; N 1.61. Found: C 71.40; H 12.07; N 1.92 (1.47% water).

The (4-hydroxycyclohexyl)-trimethylammonium p-toluenesulphonate was prepared from cis/trans-4-dimethylamino-cyclohexanol in analogy to Example 1, paragraph (a).

EXAMPLE 19

In analogy to Example 1, from 0.9 g (2.42 mmol) of (RS)-2,3-bis[[(3RS,7RS)-3,7,11-trimethyldodecyl]oxy]-propanol and 0.87 g (2.64 mmol) of (4-hydroxycyclohexyl)-trimethylammonium p-toluenesulphonate there was obtained 0.7 g (39.6%) of [(cis/trans)-4-[[[(RS)-2,3-bis[[(3RS,7RS)-3,7,11-trimethyldodecyl]oxy]propoxy]hydroxyphosphinyl]oxy]cyclohexyl]trimethylammonium hydroxide (internal salt).

NMR: 0.80–0.97 (multiplet, $CH_3$), 1.05–2.75 (broad multiplet, $CH_2$ and CH), 3.10 (singlet, $CH_3$—N), 3.35–4.15 (broad multiplet, CH—N, $CH_2$—O and CH—O).

Elementary analysis for $C_{42}H_{86}NO_6P$: Calculated: C 68.90; H 11.84; N 1.91. Found: C 68.31; H 11.49; N 1.61 (2.85% water).

EXAMPLE 20

In analogy to Example 1, from 1 g (1.72 mmol) of (RS)-1-O-[(3RS,7R,11R)-3,7,11,15-tetramethylhexyldecyl]-2-O-[(3RS,7RS)-3,7,11-trimethyldodecyl]-glycerol and 0.86 g (2.6 mmol) of (4-hydroxycyclohexyl)-trimethylammonium p-toluenesulphonate there was obtained 0.8 g (58.1%) of [(cis/trans)-4-[[hydroxy-[(RS)-3-[[(3RS,7R,11R)-3,7,11,15-tetramethylhexydecyl]oxy]-2-[[(3RS,7RS)-3,7,11-trimethyldodecyl]oxy]propoxy]phosphinyl]oxy]cyclohexyl]trimethylammonium hydroxide (internal salt).

NMR: 0.79 (multiplet, $CH_3$), 1.00–2.50 (broad multiplet, $CH_2$ and CH), 3.09 (singlet, $CH_3$—N), 3.38–3.97 (broad multiplet, CH—N, $CH_2$—O and CH—O).

Elementary analysis for $C_{47}H_{96}NO_6P$: Calculated: C 70.37; H 12.06; N 1.75. Found: C 70.00; H 12.13; N 1.99 (1.3% water).

EXAMPLE 21

In analogy to Example 1, from 1.2 g (2.34 mmol) of (RS)-2-O-[(RS)-3,7-dimethylocytl]-1-O-[(3RS,7R,11R)-3,7,11,15-tetramethylhexadecyl]glycerol and 1.16 g (3.52 mmol) of (4-hydroxycyclohexy)-trimethylammonium p-toluenesulphonate there was obtained 0.96 g (56%) of [(cis/trans)-4-[[hydroxy-[(RS)-3-[[(3RS,7R,11R)-3,7,11,15tetramethylhexadecyl]oxy]-2-[[(RS)-3,7-dimethyloctyl]oxy]propoxy]phosphinyl]oxy]cyclohexy]trimethylammonium hydroxide (internal salt).

NMR: 0.80–1.00 (multiplet, $CH_3$), 1.10–2.50 (broad multiplet, $CH_2$ and CH), 3.14 (singlet, $CH_3$—N), 3.40–4.20 (broad multiplet, CH—N, $CH_2$—0 and CH—O).

EXAMPLE 22

In analogy to Example 1, from 0.91 (1.56 mmol) of (RS)-2-O-[(3RS,7R,11R)-3,7,11,15-tetramethylhexadecyl]-1-O-[(3RS,7RS)-3,7,11-trimethyldodecyl]-glycerol and 0.8 g (2.43 mmol) of (4-hydroxycyclohexyl)-trimethylammonium p-toluenesulphonate there was obtained 0.7 g (56%) of [(cis/trans)-4-[[hydroxy-[(RS)-2-[[(3RS,7R, 11R)-3,7,11,15-tetramethylhexadecyl]oxy]-3-[[(3RS,7RS)-3,7,11,15-trimethyldodecyl]oxy]-propoxy]phosphinyl]oxy]cyclohexyl]trimethylammonium hydroxide (internal salt).

NMR: 0.78–0.93 (multiplet, $CH_3$), 1.05–2.44 (broad multiplet, $CH_2$ and CH), 3.06 (singlet, $CH_3$—N), 3.37–3.95 (broad multiplet, CH—N, $CH_2$—O and CH—O).

Elementary analysis for $C_{47}H_{96}NO_6P$: Calculated: C 70.37; H 12.06; N 1.75. Found: C 70.13; H 12.19; N 1.86 (2.57% water).

EXAMPLE 23

In analogy to Example 1, from 0.9 g (2.03 mmol) of (RS)-2-O-[(RS)-3,7-dimethyloctyl]-1-O-[(3RS,7RS)-3,7,11-trimethyldodecyl]glycerol and 1.12 g (3.4 mmol) of (4-hydroxycyclohexyl)-trimethylammonium p-toluenesulphonate there was obtained 1 g (74.3%) of [(cis/trans)-4-[[hydroxy-[(RS)-3-[[(3RS,7RS)-3,7,11-trimethyldodecyl]oxy]-2-[[(RS)-3,7-dimethyloctyl]oxy]propoxy]phosphinyl]oxy]cyclohexyl]-trimethylammonium hydroxide (internal salt).

NMR: 0.80–1.00 (multiplet, $CH_3$), 1.08–2.50 (broad multiplet, $CH_2$ and CH), 3.14 (singlet, $CH_3$—N), 3.40–4.00 (broad multiplet, CH—N, $CH_2$—O and CH—O).

Elementary analysis for $C_{37}H_{76}NO_6P$: Calculated: C 67.13; H 11.75; N 2.12. Found: C 66.76; H 11.35; N 2.05 (1.06% water).

EXAMPLE 24

In analogy to Example 1, from 0.9 g (1.76 mmol) of (RS)-1-O-[(RS)-3,7-dimethyloctyl]-2-O-[(3RS,7RS,11RS)-3,7,11,15-tetramethylhexadecyl]-glycerol and 1.2 g (3.64 mmol) of (4-hydroxycyclohexyl)-trimethylammonium p-toluenesulphonate there was obtained 0.4 g of [(cis/trans)-4-[[hydroxy-[(RS)-2-[[(3RS,7RS,11RS)-3,7,11,15-tetramethylhexadecyl]oxy]-3-[[(RS)-3,7-dimethyloctyl]oxy]propoxy]phosphinyl]oxy]cyclohexy]trimethylammonium hydroxide (internal salt).

NMR: 0.77–0.95 (multiplet, $CH_3$), 1.00–2.65 (broad multiplet, $CH_2$ and CH), 3.20 (singlet, $CH_3$—N), 3.33–4.23 (broad multiplet, CH—N, $CH_2$—O and CH—O).

Elementary analysis or $C_{42}H_{86}NO_6P$: Calculated: C 68.90: H 11.84; N 1.91. Found: C 68.62; H 11.55; N 1.74 (2.83% water).

EXAMPLE 25

In analogy to Example 1, from 1 g (2.26 mmol) of (RS)-1-O-[(RS)-dimethyloctyl]2-O-[(3RS,7RS)-3,7,11-trimethyldodecyl]glycerol and 2.1 g (6.37 mmol) of (4-hydroxycyclohexyl)-trimethylammonium p-toluenesulphonate there was obtained 0.4 g of [(cis/trans)-4-[[hydroxy-[(RS)-2-[[(3RS,7RS)-3,7,11-trimethyldodecyl]oxy]-3-[[(RS)-3,7-dimethyloctyl]oxy]propoxy]phosphinyl]oxy]cyclohexy]trimethylammonium hydroxide (internal salt).

NMR: 0.77–0.85 (multiplet, $CH_3$), 1.00–1.83 and 2.08–2.58 (2 broad multiplets, $CH_2$ and CH), 3.25 (broad singlet, $CH_3$—N), 3.33–4.25 (broad multiplet, CH—N, $CH_2$—0 and CH—O).

EXAMPLE 26

In analogy to Example 1, from 1 g (1.53 mmol) of (RS)-2,3-bis[[(3RS,7R,11R)-3,7,11,15-tetramethylhexadecyl]oxy]propanol and 1.3 g (4.3 mmol) of 4-hydroxy-1,1-dimethylpiperidinium p-toluenesulphonate there was obtained 0.5 g (38.7%) of 4-[[[(RS)-2,3-bis[[(3RS,7RS,11RS)-3,7,11,15-tetramethylhexadecyl]oxy]propoxy]hydroxyphosphinyl]oxy]-1,1-dimethylpiperidinium hyroxide (internal salt).

NMR: 0.78–0.93 (multiplet, $CH_3$), 0.97–1.72 (broad multiplet, $CH_2$ and CH, alkyl chain), 2.00–2.30 and 2.70–2.97 (2 broad multiplets, $CH_2$, ring), 3.29 (broad singlet, $CH_3$—N), 3.34–2.98 (broad multiplet, $CH_2$—N, $CH_2$—O and CH—O—P), about 4.44 (broad multiplet, CH—O).

Elementary analysis for $C_{50}H_{102}NO_6P$: Calculated: C 71.13; H 12.18; N 1.66. Found: C 70.42; H 12.03; N 1.68 (0.57% water).

The 4-hydroxy-1,1-dimethylpiperidinium p-toluenesulphonate was prepared from 4-hydroxy-1-methylpiperidine in analogy to Example 1, paragraph (a).

EXAMPLE 27

1 mmol of (s)-2,3-bis[[(3R,7R,11R)-3,7,11,15-tetramethylhexadecyl]oxy]propanol was dissolved in 7.5 ml of toluene and the solution was treated with 1.5 mmol of triethylamine and at 0° C. in the course of 30 minutes with 1.5 mmol of 2-chloro-1,3,2-dioxaphospholan-2-oxide in 2 ml of toluene. The reaction mixture was stirred at room temperature for a further 5 hours, the precipitated hydrochloride was filtered off with the exclusion of moisture and the filtrate was evaporated under reduced pressure. The residue was treated with 7.5 ml of a solution of 4 g of trimethylamine in 100 ml of acetonitrile and reacted at 70° C. overnight in a pressure flask, whereby the product precipitated partially. The solvent was removed under reduced pressure, the residue was dissolved in methanol and passed several times over 20 g of ion exchanger Amberlite MB-3. The solvent was removed and the crude product was chromatographed on silica gel with chloroform/methanol water (60:35:5). There was obtained O-[[(S)-2,3-bis[[(3R,7R,11R)-3,7,11,15-tetramethylhexadecyl]oxy]-propyl]hydroxyphosphinyl]choline hydroxide (internal salt) in a yield of 76.6%.

The NMR spectrum was almost identical with that of the product obtained in Example 1.

EXAMPLE 28

In analogy of Example 1, from (RS)-2,3-bis[[(3RS,7RS,11RS)-3,7,11,15-tetramethylhexadecyloxy]propanol and 1-[2-hydroxyethyl]-1-methylpiperidinium p-toluenesulphonate there is obtained 1-[2-[[[(RS)-2,3-bis[[(3RS,7RS,11RS)-3,7,11,15-tetramethylhexadecyl]oxy]propoxy]hydroxyphosphinyl]oxy]ethyl]-1-methylpiperidinium hydroxide (internal salt). Yield: 76%.

NMR: 0.86–0.91 (multiplet, 10 $CH_3$), 1.05–1.70 (broad multiplet, $CH_2$ and CH), 1.89–2.15 (multiplet, 3 $CH_2$ in piperidine ring), 3.18 (singlet, $CH_3$—N), 3.36–3.74, 3.88 and 4.23–4.32 (broad multiplet, triplet and multiplet, $CH_2$—O, CHO and $CH_2$—N).

The 1-[2-hydroxyethyl]-1-methyl-piperidinium p-toluenesulphonate can be obtained from 1-(2-hydroxyethyl)-piperidine in analogy to Example 1(a).

EXAMPLE 29

In analogy to Example 1, from (RS)-2-O-[octadecyl]-1-O-[(3RS,7RS,11RS)-3,7,11,15-tetramethylhexadecyl]-glycerol and choline tosylate there is obtained O-[hydroxy[(RS)-2-[[octadecyl]oxy]-3-[[(3RS,7RS,11RS)-3,7,11,15-tetramethylhexadecyl]oxy]propoxy]phosphinyl]choline hydroxide (internal salt).

NMR: 0.83–0.93 (multiplet, 6 $CH_3$), 1.0–1.68 (broad multiplet, $CH_2$ and CH), 3.22 (singlet, $CH_3$—N), 3.41–3.70, 3.90 and 4.21–4.33 (broad multiplet, triplet and multiplet, $CH_2O$, CHO and $CH_2$—N).

The starting material can be obtained from (RS)-1-O-[(3RS,7RS,11RS)-3,7,11,15-tetramethylhexadecyl]-3-O- tritylglycerol and n-octadecyl p-toluenesulphonate in analogy to Example 4(d) and (e).

EXAMPLE 30

In analogy to Example 1, from 1,3-bis[[(3RS,7RS,11RS)-3,7,11,15-tetramethylhexadecyl]oxy]propan-2 ol and choline tosylate there is obtained O-[[1,3-bis[[(3RS,7RS,11RS)-3,7,11,15-tetramethylhexadecyl]oxy]isopropyl]hydroxyphosphinyl]choline hydroxide (internal salt).

NMR: 0.85–0.92 (multiplet, 10 $CH_3$), 1.0–1.68 (multiplet, $CH_2$ and CH), 3.22 (singlet, $CH_3$—N), 3.43–3.58 and 3.58–3.67 (2 multiplets, $CH_2$—O and $CH_2N$), 4.24–4.41 (multiplet, CH—O—P—O—$CH_2$).

The starting material can be prepared as follows:

(a) (RS)-1-O-[(3RS,7RS,11RS)-3,7,11,15-Tetramethylhexadecyl]glycerol is obtained in analogy to Example 4(b).

(b) The glycerol derivative obtained in (a) is monotosylated to give [(RS)-3-[[(3RS,7RS,11RS)-3,7,11,15-tetramethylhexadecyl]oxy]-2-hydroxy]propyl p-toluenesulphonate.

(c) The toluenesulphonate obtained in (b) is reacted at 90° C. with a five-fold molar amount of dihydrophytol in which a 1.2-fold molar amount of sodium hydride has previously been dissolved. After completion of the reaction the excess dihydrophytol and the sodium p-toluenesulphonate are separated from 1,3-bis[[(3RS,7RS,11RS)-3,7,11,15-tetramethylhexadecyl]oxy]propan-2-ol.

EXAMPLE 31

In analogy to Example 1, from (RS)-1-O-[octadecyl]-3-O-[(3RS,7RS,11RS)-3,7,11,15-tetramethylhexadecyl]-glycerol and choline tosylate there is obtained O-[hydroxy[(RS)-1-[[octadecyl]oxy]-3-[[(3RS,7RS,11RS)-3,7,11,15 -tetramethylhexadecyl]oxy]isopropoxy]phosphinyl]choline hydroxide (internal salt).

NMR: 0.84–0.91 (multiplet, 6 $CH_3$), 1.0–1.45, 1.27 and 1.45–1.67 (multiplet, singlet and multiplet, $CH_2$ and CH), 3.22 (singlet, $CH_3N$), 3.04–3.70 (multiplet, $CH_2$—N and $CH_2$—O), 4.23–4.42 (multiplet, CH—O—P—$OCH_2$).

The starting material can be obtained in analogy to Example 30(c) using octadecanol in place of dihydrophytol.

EXAMPLE 32

1.0 g of the compound manufactured in Example 10, 2.4 g of saccharose and 7.5 ml of water are stirred intensively with a magnetic stirrer for 1 hour. Thereby there results a milky dispersion which contains mainly multilamellar liposomes.

This dispersion is subsequently treated with ultrasound (Branson Sonifier B-12) or 20 minutes (at 20° C., pH 7.0 and under $N_2$ gasification), whereby there forms a slightly opalescent liposome solution which consists for the most part of small monolamellar liposomes.

In order to remove the coarsest particles, the solution is subsequently centrifuged and filtered through a 0.22μ millipore filter. It is then filled into ampoules and heat-sterilized (20 minutes at 120° C.).

EXAMPLE 33

4.1 mg/ml of diazepam are dissolved by stirring in the slightly opalescent liposome solution obtained in Example 32 prior to the filtration. Processing is subsequently continued as above. There is thus obtained a diazepam injection solution which is stable for months.

EXAMPLE 34

0.78 g of Na glycocholate and 1.02 g of the compound manufactured in Example 10 are dissolved in 10 ml of methanol. By rapid evaporation in vacuo there is produced from this solution on the wall of a flask a thin film. This is again dissolved by the addition of 8.38 ml of water, whereby a clear mixed micelle solution results.

After filtration through a 0.22μ millipore filter the micelle solution is filled into ampoules and sterilized (20 minutes at 120° C.).

What is claimed:

1. A compound of the formula

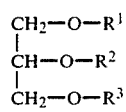

wherein two of the residues $R^1$, $R^2$ and $R^3$ represent $C_{10-30}$-alkyl residues with at least 8 C-atoms in a straight chain, at least one of these residues being substituted by at least 2 $C_{1-3}$-alkyl residues and the sum of the C-atoms in the two residues being greater than 20; and the third residue is a residue —P(O)($O^-$)$OR^4$ in which $R^4$ is $C_{5-7}$-cycloalkyl residue which is substituted by a quaternary ammonium group or a $C_{5-7}$-cycloalkyl residue which contains a di-(lower-alkyl)-substituted nitrogen atom.

2. A compound in accordance with claim 1, in which $R^1$ and $R^2$ represent $C_{10-30}$-alkyl residues with at least 8 C-atoms in a straight-chain, each of which is substituted by at least 2 $C_{1-3}$-alkyl residues.

3. A compound in accordance with claim 2, wherein two of the residues $R^1$, $R^2$ and $R^3$ represent residues of the formula

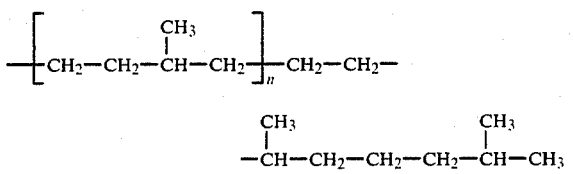

wherein n is a whole number of 0—4.

4. A compound in accordance with claim 3, in which two of the residues $R^1$, $R^2$ and $R^3$ represent tetrahydrogeranyl, hexahydrofarnesyl or dihydrophytyl.

5. A compound in accordance with claim 4, in which $R^4$ is tri-(lower-alkyl)-ammonio-$C_{5-7}$-cycloalkyl or N,N-di-lower-alkyl-$C_{4-6}$-azacycloalkyl.

6. A compound in accordance with claim 5, in which $R^4$ is 4-(trimethylammonio)cyclohexyl or N,N-dimethyl-4-piperidyl.

7. A compound in accordance with claim 1, [(cis/trans)-4-[[[(RS)-2,3-bis[[(3RS,7R,11R)-3,7,11,15-tetramethylhexadecyl]oxy]propoxy]hydroxyphosphinyl]oxy]cyclohexyl]trimethylammonium hydroxide (internal salt).

* * * * *

UNITED STATES PATENT AND TRADEMARK OFFICE
CERTIFICATE OF CORRECTION

PATENT NO. : 4,694,084
DATED : September 15, 1987
INVENTOR(S) : Manfred Breuninger and Dieter Schmidt It is certified that error appears in the above-identified patent and that said Letters Patent are hereby corrected as shown below:

In claim 1, line 8 delete "-P(O)(O-)OR$^4$" and insert therefor -- -P(O)(O$^-$)OR$^4$ --.

In claim 3, lines 3 and 4 delete $-[CH_2-CH_2-\underset{\underset{CH_3}{|}}{CH}-CH_2]_n-CH_2-CH_2-\underset{\underset{CH_3}{|}}{CH}-CH_2-CH_2-CH_2-\underset{\underset{CH_3}{|}}{CH}-CH_3$ and insert therefor $--[CH_2-CH_2-\underset{\underset{CH_3}{|}}{CH}-CH_2]_n-CH_2-CH_2-\underset{\underset{CH_3}{|}}{CH}-CH_2-CH_2-CH_2-\underset{\underset{CH_3}{|}}{CH}-CH_3 --.$ Signed and Sealed this Seventh Day of June, 1988

Attest:

DONALD J. QUIGG

Attesting Officer

Commissioner of Patents and Trademarks